(12) United States Patent
Krimsky

(10) Patent No.: US 11,622,815 B2
(45) Date of Patent: *Apr. 11, 2023

(54) SYSTEMS AND METHODS FOR PROVIDING PROXIMITY AWARENESS TO PLEURAL BOUNDARIES, VASCULAR STRUCTURES, AND OTHER CRITICAL INTRA-THORACIC STRUCTURES DURING ELECTROMAGNETIC NAVIGATION BRONCHOSCOPY

(71) Applicant: Covidien LP, Mansfield, MA (US)

(72) Inventor: William S. Krimsky, Forest Hill, MD (US)

(73) Assignee: Covidien LP, Mansfield, MA (US)

( * ) Notice: Subject to any disclaimer, the term of this patent is extended or adjusted under 35 U.S.C. 154(b) by 256 days.

This patent is subject to a terminal disclaimer.

(21) Appl. No.: 17/164,892

(22) Filed: Feb. 2, 2021

(65) Prior Publication Data

US 2021/0153955 A1 May 27, 2021

Related U.S. Application Data

(63) Continuation of application No. 15/254,100, filed on Sep. 1, 2016, now Pat. No. 10,939,963.

(51) Int. Cl.
*A61B 34/20* (2016.01)
*A61B 5/06* (2006.01)
(Continued)

(52) U.S. Cl.
CPC ............ *A61B 34/20* (2016.02); *A61B 1/2676* (2013.01); *A61B 5/066* (2013.01); *A61B 5/1135* (2013.01);
(Continued)

(58) Field of Classification Search
None
See application file for complete search history.

(56) References Cited

U.S. PATENT DOCUMENTS 7,985,187 B2  7/2011  Wibowo et al.
8,494,246 B2  7/2013  Trumer et al.
(Continued)

FOREIGN PATENT DOCUMENTS

WO  2008103383 A1  8/2008
WO  2014194167 A1  12/2014
WO  2015044901 A1  4/2015

OTHER PUBLICATIONS

Franz, A. M., Haidegger, T., Birkfellner, W., Cleary, K., Peters, T. M., & Maier-Hein, L. (2014). Electromagnetic tracking in medicine—A review oftechnology, validation, and applications. IEEE transactions on medical imaging, 33(8), 1702-1725. (Year: 2014).

(Continued)

*Primary Examiner* — Yi-Shan Yang
(74) *Attorney, Agent, or Firm* — Carter, DeLuca & Farrell LLP

(57) ABSTRACT

Disclosed are systems, devices and methods for providing proximity awareness to an anatomical feature while navigating inside a patient's chest, an exemplary method including receiving image data of the patient's chest, generating a three-dimensional (3D) model of the patient's chest based on the received image data, determining a location of the anatomical feature based on the received image data and the generated 3D model, tracking a position of an electromagnetic sensor included in a tool, iteratively determining a position of the tool inside the patient's chest based on the tracked position of the electromagnetic sensor, and indicating a proximity of the tool relative to the anatomical feature, based on the determined position of the tool inside the patient's chest.

20 Claims, 8 Drawing Sheets

(51) Int. Cl.
| | |
|---|---|
| *G06T 7/73* | (2017.01) |
| *A61B 34/10* | (2016.01) |
| *A61B 34/00* | (2016.01) |
| *A61B 90/00* | (2016.01) |
| *A61B 1/267* | (2006.01) |
| *A61B 5/113* | (2006.01) |
| *A61B 6/03* | (2006.01) |
| *A61B 10/02* | (2006.01) |
| *G06T 15/20* | (2011.01) |
| *G06T 19/20* | (2011.01) |
| *A61B 17/00* | (2006.01) |
| *A61B 5/00* | (2006.01) |
| *A61B 5/055* | (2006.01) |
| *A61B 18/18* | (2006.01) |

(52) U.S. Cl.
CPC .............. *A61B 6/032* (2013.01); *A61B 6/037* (2013.01); *A61B 10/02* (2013.01); *A61B 34/10* (2016.02); *A61B 34/25* (2016.02); *A61B 90/37* (2016.02); *G06T 7/75* (2017.01); *G06T 15/205* (2013.01); *G06T 19/20* (2013.01); *A61B 5/055* (2013.01); *A61B 5/721* (2013.01); *A61B 18/1815* (2013.01); *A61B 2017/00115* (2013.01); *A61B 2017/00699* (2013.01); *A61B 2017/00809* (2013.01); *A61B 2034/102* (2016.02); *A61B 2034/105* (2016.02); *A61B 2034/107* (2016.02); *A61B 2034/2051* (2016.02); *A61B 2090/061* (2016.02); *A61B 2090/08021* (2016.02); *A61B 2090/367* (2016.02); *A61B 2090/378* (2016.02); *G06T 2210/41* (2013.01)

(56) References Cited

U.S. PATENT DOCUMENTS

| | | | |
|---|---|---|---|
| 8,611,983 | B2 | 12/2013 | Glossop |
| 8,696,549 | B2 | 4/2014 | Holsing et al. |
| 8,696,685 | B2 | 4/2014 | Gilboa |
| 8,700,132 | B2 | 4/2014 | Ganatra et al. |
| 9,259,290 | B2 | 2/2016 | Jenkins et al. |
| 9,439,564 | B2 | 9/2016 | Trumer et al. |
| 9,459,770 | B2 | 10/2016 | Baker |
| 10,939,963 | B2 | 3/2021 | Krimsky |
| 2002/0045809 | A1 | 4/2002 | Ben-Haim |
| 2003/0093067 | A1 | 5/2003 | Panescu |
| 2005/0027194 | A1 | 2/2005 | Adler et al. |
| 2005/0197558 | A1 | 9/2005 | Williams et al. |
| 2006/0116576 | A1 | 6/2006 | McGee et al. |
| 2007/0083194 | A1 | 4/2007 | Kunis |
| 2008/0243142 | A1* | 10/2008 | Gildenberg ............ G16H 30/40 606/130 |
| 2009/0227861 | A1 | 9/2009 | Ganatra et al. |
| 2010/0312095 | A1 | 12/2010 | Jenkins et al. |
| 2012/0059248 | A1 | 3/2012 | Holsing et al. |
| 2012/0289815 | A1 | 11/2012 | Keast |
| 2013/0165915 | A1 | 6/2013 | Thiel |
| 2014/0031820 | A1 | 1/2014 | Whayne |
| 2014/0187949 | A1 | 7/2014 | Zhao et al. |
| 2014/0228632 | A1 | 8/2014 | Sholev |
| 2014/0343408 | A1 | 11/2014 | Tolkowsky |
| 2015/0005757 | A1* | 1/2015 | Wang ................. A61B 18/1815 606/33 |
| 2015/0227680 | A1 | 8/2015 | Mainkar |
| 2015/0265368 | A1 | 9/2015 | Chopra et al. |
| 2015/0305650 | A1 | 10/2015 | Hunter et al. |
| 2016/0000303 | A1 | 1/2016 | Klein et al. |
| 2016/0015453 | A1 | 1/2016 | van der Weide et al. |
| 2016/0228175 | A1 | 8/2016 | Sliwa |

OTHER PUBLICATIONS

Wong, S., Zaremba, L., Gooden, D., & Huang, H. K. (1995) Radiologic image compression—a review. Proceedings of the IEEE, 83( 2), 194-219. (Year: 1995).

Extended European Search Report for application No. 17188613.8 dated Nov. 13, 2017 (9 pages).

European Examination Report issued in Appl. No. EP 17188613.8-1122 dated Jan. 2, 2019 (10 pages).

* cited by examiner

SYSTEMS AND METHODS FOR PROVIDING PROXIMITY AWARENESS TO PLEURAL BOUNDARIES, VASCULAR STRUCTURES, AND OTHER CRITICAL INTRA-THORACIC STRUCTURES DURING ELECTROMAGNETIC NAVIGATION BRONCHOSCOPY

CROSS-REFERENCE TO RELATED APPLICATIONS

This application is a continuation of U.S. patent application Ser. No. 15/254,100, filed on Sep. 1, 2016, the entire contents of which being incorporated by reference herein.

FIELD

The present disclosure relates to navigation of surgical tools within a patient's chest, and more specifically, to systems and methods for providing proximity awareness to pleural boundaries of the patient's lungs and vascular structures while navigating the patient's chest.

BACKGROUND

Early stage diagnosis is one of many important facets in the battle against lung cancer. The National Lung Screening Trial has demonstrated that a reduction in mortality occurs if diagnostic scans, such as computed tomography (CT) scans, are used for early detection for those at risk of contracting the disease. While CT scans increase the possibility that small lesions and nodules in the lung can be detected, these lesions and nodules still require biopsy and cytological examination before a diagnosis can be rendered and treatment can be undertaken.

To perform a biopsy, as well as with many other treatments, navigation of tools within the lungs to a target location, such as the point of biopsy or treatment, is necessary. For example, bronchoscopy is a medical procedure used to diagnose and treat various lung diseases by navigating one or more tools into the airways of the patient's lungs. The pleura, or pleural surfaces, form the outer boundaries of the patient's lungs and are composed of two serous membranes: the outer parietal pleura line the inner wall of the rib cage, and the inner visceral pleura directly line the surface of the lungs. Injuries, such as pneumothorax and pneumomediastinum may be attributed to a tool puncturing, injuring, or violating the visceral pleural surface. This danger, therefore, would also apply to any vascular or other critical intra-thoracic structure that might be injured that are in the area or interposed between the tools and the target or area of interest. Thus, to reduce the potential for injury, improvements to systems and methods of navigating are continually being sought.

SUMMARY

Provided in accordance with the present disclosure is a method for providing proximity awareness to an anatomical feature while navigating inside a patient's chest. In an aspect of the present disclosure, the method includes receiving image data of the patient's chest, generating a three-dimensional (3D) model of the patient's chest based on the received image data, determining a location of the anatomical feature based on the received image data and the generated 3D model, tracking a position of an electromagnetic sensor included in a tool, iteratively determining a position of the tool inside the patient's chest based on the tracked position of the electromagnetic sensor, and indicating a proximity of the tool relative to the anatomical feature, based on the determined position of the tool inside the patient's chest.

In another aspect of the present disclosure, the method further includes determining whether the tool is within a predetermined distance from the anatomical feature, and providing a proximity alert, in response to a determination that the tool is within the predetermined distance from the anatomical feature.

In a further aspect of the present disclosure, the method further includes receiving data corresponding to movement of the patient's chest based on the patient's respiratory cycle, and wherein determining whether the tool is within the predetermined distance from the anatomical feature includes determining whether the tool is within the predetermined distance from the anatomical feature based on the data regarding movement of the patient's chest.

In another aspect of the present disclosure, the method further includes receiving data corresponding to movement of the patient's chest based on the patient's respiratory cycle, and wherein determining the location of the anatomical feature includes determining the location of the anatomical feature based on the data corresponding to the movement of the patient's chest.

In a further aspect of the present disclosure, the anatomical feature is a pleural surface of the patient's lungs.

In another aspect of the present disclosure, the anatomical feature is a vascular structure.

In a further aspect of the present disclosure, the method further includes receiving additional image data of the patient's chest, and updating the 3D model based on the additional image data.

In another aspect of the present disclosure, the indicating the proximity of the tool relative to the anatomical feature includes displaying a distance between the tool and the anatomical feature, and a direction of the tool relative to the anatomical feature.

Provided in accordance with the present disclosure is a system for providing proximity awareness to an anatomical feature while navigating inside a patient's chest. In an aspect of the present disclosure, the system includes an electromagnetic navigation system including an electromagnetic field generator, a tool configured to be inserted into the patient's chest, and an electromagnetic sensor disposed on the tool, and a computing device including a processor and a memory storing instructions which, when executed by the processor, cause the computing device to receive image data of the patient's chest, generate a three-dimensional (3D) model of the patient's chest based on the received image data, determine a location of the anatomical feature based on the received image data and the generated 3D model, track a position of the electromagnetic sensor, iteratively determine a position of the tool inside the patient's chest based on the tracked position of the electromagnetic sensor, and provide instructions to indicate a proximity of the tool relative to the anatomical feature, based on the determined position of the tool inside the patient's chest.

In another aspect of the present disclosure, the instructions further cause the computing device to determine whether the tool is within a predetermined distance from the anatomical feature, and provide a proximity alert when a determination is made that the tool is within the predetermined distance from the anatomical feature.

In a further aspect of the present disclosure, the instructions further cause the computing device to receive data corresponding to movement of the patient's chest based on the patient's respiratory cycle, and wherein the computing device determines whether the tool is within the predetermined distance from the anatomical feature by determining whether the tool is within the predetermined distance from the anatomical feature based on the data regarding movement of the patient's chest.

In another aspect of the present disclosure, the instructions further cause the computing device to receive data corresponding to movement of the patient's chest based on the patient's respiratory cycle, and wherein the computing device determines the location of the anatomical feature by determining the location of the anatomical feature based on the data corresponding to the movement of the patient's chest.

In a further aspect of the present disclosure, the anatomical feature is a pleural surface of the patient's lungs.

In another aspect of the present disclosure, the anatomical feature is a vascular structure.

In a further aspect of the present disclosure, the instructions further cause the computing device to receive additional image data of the patient's chest, and update the 3D model based on the additional image data.

In another aspect of the present disclosure, the indication of the proximity of the tool relative to the anatomical feature includes a distance between the tool and the anatomical feature, and a direction of the tool relative to the anatomical feature.

Provided in accordance with the present disclosure is a non-transitory computer-readable storage medium storing instructions for providing proximity awareness to an anatomical feature while navigating inside a patient's chest. In an aspect of the present disclosure, the instructions, when executed by a processor, cause a computer to receive image data of the patient's chest, generate a three-dimensional (3D) model of the patient's chest based on the received image data, determine a location of the anatomical feature based on the received image data and the generated 3D model, track a position of the electromagnetic sensor, iteratively determine a position of the tool inside the patient's chest based on the tracked position of the electromagnetic sensor, and provide instructions indicate a proximity of the tool relative to the anatomical feature, based on the determined position of the tool inside the patient's chest.

In another aspect of the present disclosure, the instructions further cause the computer to determine whether the tool is within a predetermined distance from the anatomical feature, and provide a proximity alert when a determination is made that the tool is within the predetermined distance from the anatomical feature.

In a further aspect of the present disclosure, the instructions further cause the computer to receive additional image data of the patient's chest, and update the 3D model based on the additional image data.

In another aspect of the present disclosure, the indication of the proximity of the tool relative to the anatomical feature includes a distance between the tool and the anatomical feature, and a direction of the tool relative to the anatomical feature.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Methods, systems, and computer-readable media for providing proximity awareness to intra-thoracic structures, pleural boundaries, and vascular structures during tool navigation inside a patient's chest are provided in accordance with the present disclosure.

The methods, systems, and computer-readable media described herein are useful in various planning and/or navigation contexts for procedures performed on the patient's chest. For example, in an embodiment in which a clinician is performing a bronchoscopy, the methods and systems may alert the clinician as to the proximity of the tools relative to the patient's pleural surfaces. Additionally, as will be described in further detail below, in configurations of the system in which a location sensor is incorporated into a tool and/or catheters to track the location and assist in navigation of the tools, the tracked location of the location sensor may be used to visually show the location of the tools on a three-dimensional (3D) model of the patient's chest and the proximity of the tools relative to the target location. Moreover, by providing the location of the location sensor within the body of a patient with reference to the 3D model and/or two-dimensional (2D) images along with a planned pathway, the clinician may be able to navigate about the lungs of the patient with improved proximity awareness to such pleural boundaries and vascular structures to thereby permit the clinician to exercise additional caution during a procedure. These and other aspects of the present disclosure are detailed herein below.

Methods for proximity awareness to pleural boundaries and vascular structures may be implemented via an electromagnetic navigation (EMN) system. Generally, in an embodiment, the EMN system may be used in planning a pathway the target location, navigating a positioning assembly to the target location, and navigating a variety of tools, such as a locatable guide (LG) and/or a treatment tool, such as a biopsy tool or an ablation tool, to the target location. The EMN system may be configured to display various views of the patient's body, and of the aforementioned 3D model.

Figure 1:
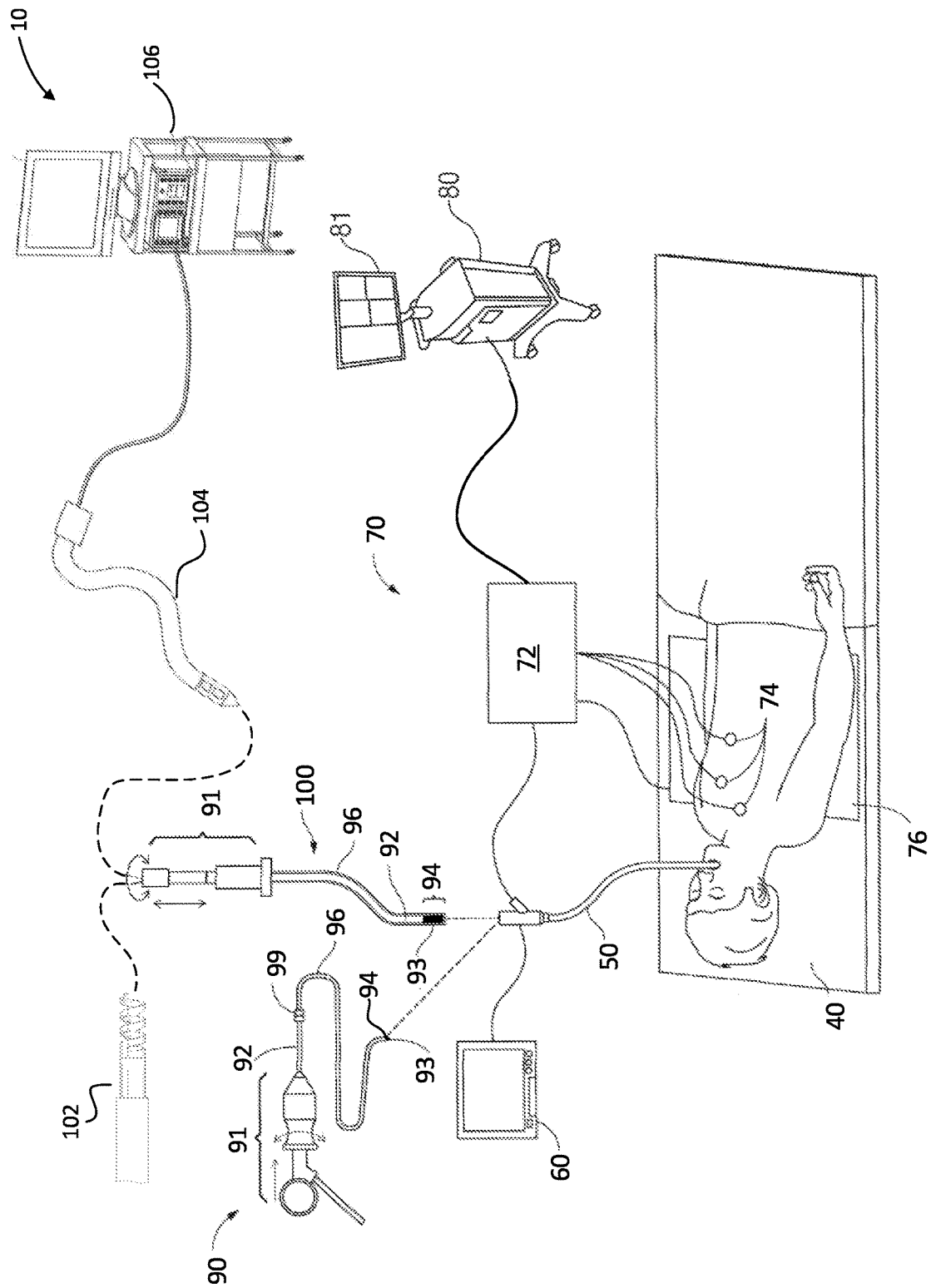
FIG. 1 is a system diagram of an electromagnetic navigation (EMN) system, which may be used to provide proximity awareness to pleural boundaries and vascular structures, according to an embodiment of the present disclosure.

With reference to FIG. 1, an endobronchial EMN system 10 suitable for implementing methods for proximity awareness to pleural boundaries and vascular structures is provided in accordance with the present disclosure. One such EMN system 10 is the ELECTROMAGNETIC NAVIGATION BRONCHOSCOPY® system currently sold by Covidien LP. As shown in FIG. 1, EMN system 10 is used to perform one or more procedures on a patient supported on an operating table 40. In this regard, EMN system 10 generally includes a bronchoscope 50, monitoring equipment 60, an electromagnetic (EM) tracking system 70, and a computing device 80.

Bronchoscope 50 is configured for insertion through the patient's mouth and/or nose into the patient's airways. As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, for example, a video display, for displaying the video images received from the video imaging system of bronchoscope 50.

In an embodiment, bronchoscope 50 may operate in conjunction with a catheter guide assembly, two types of which are depicted in FIG. 1 (for example, catheter guide assemblies 90, 100). Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). Although configured differently, catheter guide assemblies 90, 100 share a number of common components. Specifically each catheter guide assembly 90, 100 includes a handle 91, which is connected to an extended working channel (EWC) 96. In each assembly 90, 100, EWC 96 is sized for placement into the working channel of bronchoscope 50. In the operation of each assembly 90, 100, a locatable guide (LG) 92, including an EM sensor 94, is inserted into EWC 96 and locked into position such that EM sensor 94 extends a desired distance beyond the distal tip 93 of EWC 96. The location of EM sensor 94, and thus the distal end of EWC 96, within an EM field generated by EM field generator 76 can be derived by tracking module 72, and computing device 80. Catheter guide assemblies 90, 100 may have different operating mechanisms, but each includes handle 91 that can be manipulated by rotation and compression to steer distal tip 93 of LG 92 and EWC 96.

Catheter guide assembly 90 is currently marketed and sold by Covidien LP under the name SUPERDIMENSION® Procedure Kits. Catheter guide assembly 100 is currently sold by Covidien LP under the name EDGE™ Procedure Kits. Both kits include handle 91, EWC 96, and LG 92. For a more detailed description of catheter guide assemblies 90, 100, reference is made to commonly-owned U.S. Pat. No. 9,247,992, entitled "MICROWAVE ABLATION CATHETER AND METHOD OF UTILIZING THE SAME", filed on Mar. 15, 2013 by Ladtkow et al., the entire contents of which are hereby incorporated by reference.

LG 92 and EWC 96 are selectively lockable relative to one another via a locking mechanism 99. A six degrees-of-freedom EM tracking system 70, e.g., similar to those disclosed in U.S. Pat. No. 6,188,355 and published PCT Application Nos. WO 00/10456 and WO 01/67035, entitled "WIRELESS SIX-DEGREE-OF-FREEDOM LOCATOR", filed on Dec. 14, 1998 by Gilboa, the entire contents of each of which is incorporated herein by reference, or any other suitable positioning measuring system, is utilized for performing navigation, although other configurations are also contemplated.

EM tracking system 70 may be configured for use with catheter guide assemblies 90, 100 to track the position of EM sensor 94 as it moves in conjunction with EWC 96 through the airways of the patient, as detailed below. In an embodiment, EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The six degrees of freedom coordinates of reference sensors 74 are sent as data to computing device 80, which includes application 81, where the data from sensors 74 are used to calculate a patient coordinate frame of reference.

Although EM sensor 94 is described above as being included in LG 92 it is also envisioned that EM sensor 94 may be embedded or incorporated within a biopsy tool 102 where biopsy tool 102 may alternatively be utilized for navigation without need of LG 92 or the necessary tool exchanges that use of LG 92 requires. Similarly, it is envisioned that EM sensor 94 may be embedded or incorporated within a microwave ablation tool 104, where microwave ablation tool 104 may alternatively be utilized for navigation without the need of LG 92 or the necessary tool exchanges that use of LG 92 requires.

According to an embodiment, biopsy tool 102 is configured to be insertable into catheter guide assemblies 90, 100 following navigation to a target location and removal of LG 92. Biopsy tool 102 may be used to collect one or more tissue samples from the target location, and in an embodiment, is further configured for use in conjunction with tracking system 70 to facilitate navigation of biopsy tool 102 to the target location, and tracking of a location of biopsy tool 102 as it is manipulated relative to the target location to obtain the tissue sample. Similarly, microwave ablation tool 104 is configured to be insertable into catheter guide assemblies 90, 100 following navigation to a target location and removal of LG 92. Microwave ablation tool 104 is configured to be operated with a microwave generator 106, and may include any of a variety of microwave ablation tools and/or catheters, examples of which are more fully described in U.S. Pat. Nos. 9,259,269; 9,247,993; 9,044,254; 9,370,398; and 9,993,295, the entire contents of each of which is incorporated herein by reference. Though shown as a biopsy tool and microwave ablation tool in FIG. 1, those of skill in the art will recognize that other tools including for example RF ablation tools, brachytherapy tools, and others may be similarly deployed and tracked without departing from the scope of the present disclosure.

For example, a variety of useable biopsy tools are described in U.S. Patent Publication No. 2015/0141809, entitled "DEVICES, SYSTEMS, AND METHODS FOR NAVIGATING A BIOPSY TOOL TO A TARGET LOCATION AND OBTAINING A TISSUE SAMPLE USING THE SAME", filed Sep. 17, 2014, by Costello et al., and U.S. Pat. No. 10,278,680, entitled "DEVICES, SYSTEMS, AND METHODS FOR NAVIGATING A BIOPSY TOOL TO A TARGET LOCATION AND OBTAINING A TISSUE SAMPLE USING THE SAME", filed Dec. 9, 2014, by Costello et al., the contents of each of which are incorporated herein by reference and useable with the EMN system 10 as described herein.

Computing device 80 includes software and/or hardware, such as an EMN application 81, used to facilitate the various phases of an EMN procedure, including generating the 3D model, identification of a target location, planning a pathway to the target location, registration of the 3D model with the patient's actual airways, and navigation to the target location. For example, during procedure planning, computing device 80 utilizes computed tomographic (CT) scan, magnetic resonance imaging (MM) scan, X-ray scan, cone beam computed tomography (CBCT) scan, and/or positron emission tomography (PET) scan image data for generating and viewing the 3D model of the patient's airways, enables the identification of a target location on the 3D model (automatically, semi-automatically or manually), and allows for the determination and selection of a pathway through the patient's airways to the target location. While the CT scan image data may have gaps, omissions, and/or other imperfections included in the image data, the 3D model is a smooth representation of the patient's airways, with any such gaps, omissions, and/or imperfections in the CT scan image data filled in or corrected. The 3D model may be presented on a display monitor associated with computing device 80, or in any other suitable fashion. An example of the planning software described herein can be found in U.S. Pat. Nos. 9,459,770, 9,925,009, and 9,639,666, filed by Baker et al. on Mar. 15, 2013, and entitled "PATHWAY PLANNING SYSTEM AND METHOD", the contents of all of which are incorporated herein by reference. Further examples of the planning software can be found in commonly assigned U.S. Pat. No. 9,770,216, entitled "SYSTEM AND METHOD FOR NAVIGATING WITHIN THE LUNG", filed on Jun. 29, 2015, by Brown et al., the contents of which are incorporated herein by reference.

Using computing device 80, various views of the 3D model may be presented and may be manipulated by a clinician to facilitate identification of a target location and selection of a suitable pathway through the patient's airways to access the target location. The 3D model may include, among other things, a model airway tree corresponding to the actual airways of the patient's lungs, and showing the various passages, branches, and bifurcations of the patient's actual airway tree. Additionally, the 3D model may include lesions, markers, blood vessels and vascular structures, lymphatic vessels and structures, organs, other physiological structures, and/or a 3D rendering of the pleura. Some or all of the aforementioned elements may be selectively displayed, such that the clinician may choose which elements should be displayed during when viewing the 3D model. For example, EMN application 81 may be configured in various states to display the 3D model in a variety of view modes. For each view of the 3D model, the angle from which the 3D model is displayed may correspond to a view point. The view point may be fixed at a predefined location and/or orientation, or may be adjusted by the clinician operating computing device 80.

Following pathway planning, a procedure may be undertaken in which EM sensor 94, in conjunction with tracking system 70, enables tracking of EM sensor 94 (and thus the distal end of EWC 96 or tool 102) as EM sensor 94 is advanced through the patient's airways following the pathway planned during the pathway planning phase. As an initial step of the procedure, the 3D model is registered with the patient's actual airways. One potential method of registration involves navigating a locatable guide into each lobe of the patient's lungs to at least the second bifurcation of the airways of that lobe. The position of the locatable guide is tracked during this registration phase, and the 3D model is iteratively updated based on the tracked position of the locatable guide within the actual airways of the patient's lungs. This registration process is described in commonly-owned U.S. Patent Application Publication No. 2011/0085720, entitled "AUTOMATIC REGISTRATION TECHNIQUE," filed on May 14, 2010, by Barak et al., and U.S. Pat. No. 10,772,532, entitled "REAL-TIME AUTOMATIC REGISTRATION FEEDBACK", filed on Jul. 2, 2015, by Brown et al., the contents of each of which are incorporated herein by reference. While the registration process focuses on aligning the patient's actual airways with the airways of the 3D model, registration also ensures that the position of vascular structures and the pleura are accurately determined.

Figure 2:
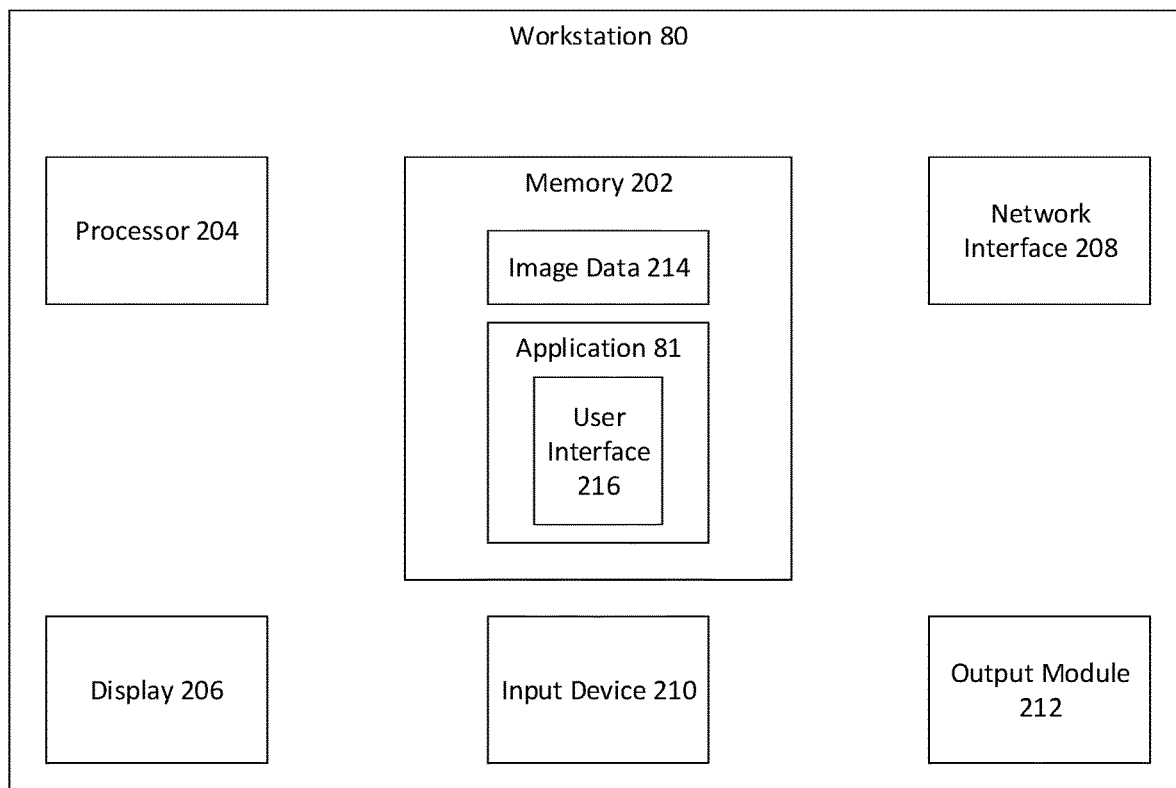
FIG. 2 is a schematic diagram of a computing device forming part of the EMN system of FIG. 1, which may be used to provide proximity awareness to pleural boundaries and vascular structures, according to an embodiment of the present disclosure.

Turning now to FIG. 2, computing device 80 may include a memory 202, a processor 204, a display 206, a network interface 208, an input device 210, and/or an output module 212. Memory 202 may store application 81 and/or image data 214. Application 81 may, when executed by processor 204, cause display 206 to present user interface 216. Application 81 may also provide the interface between the sensed position of EM sensor 94 and the image and planning data developed in the pathway planning phase.

Figure 3A:
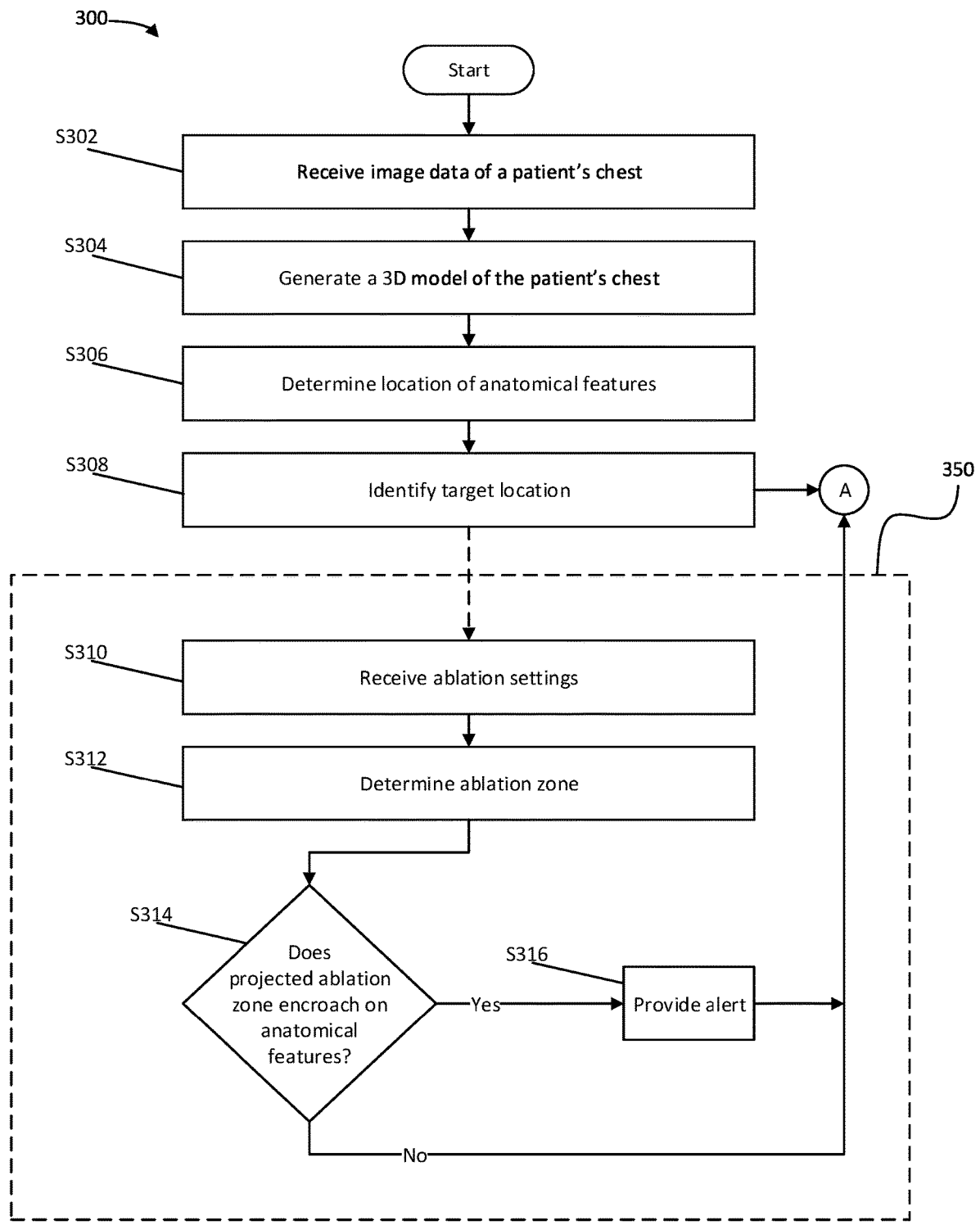
FIGS. 3A-3C is a flowchart illustrating a method for providing proximity awareness to pleural boundaries and vascular structures, according to an embodiment of the present disclosure.
Figure 3B:
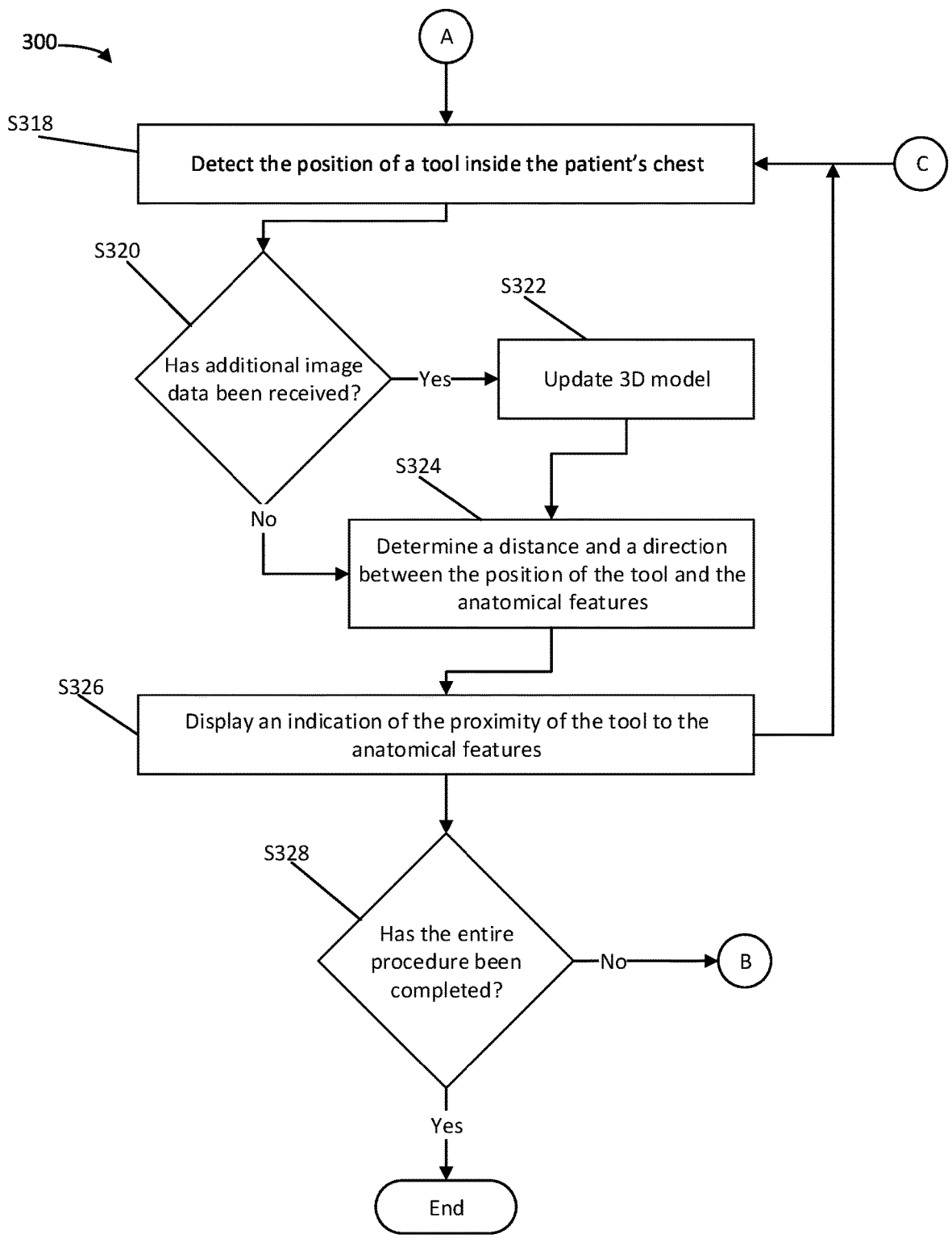
Figure 3C:
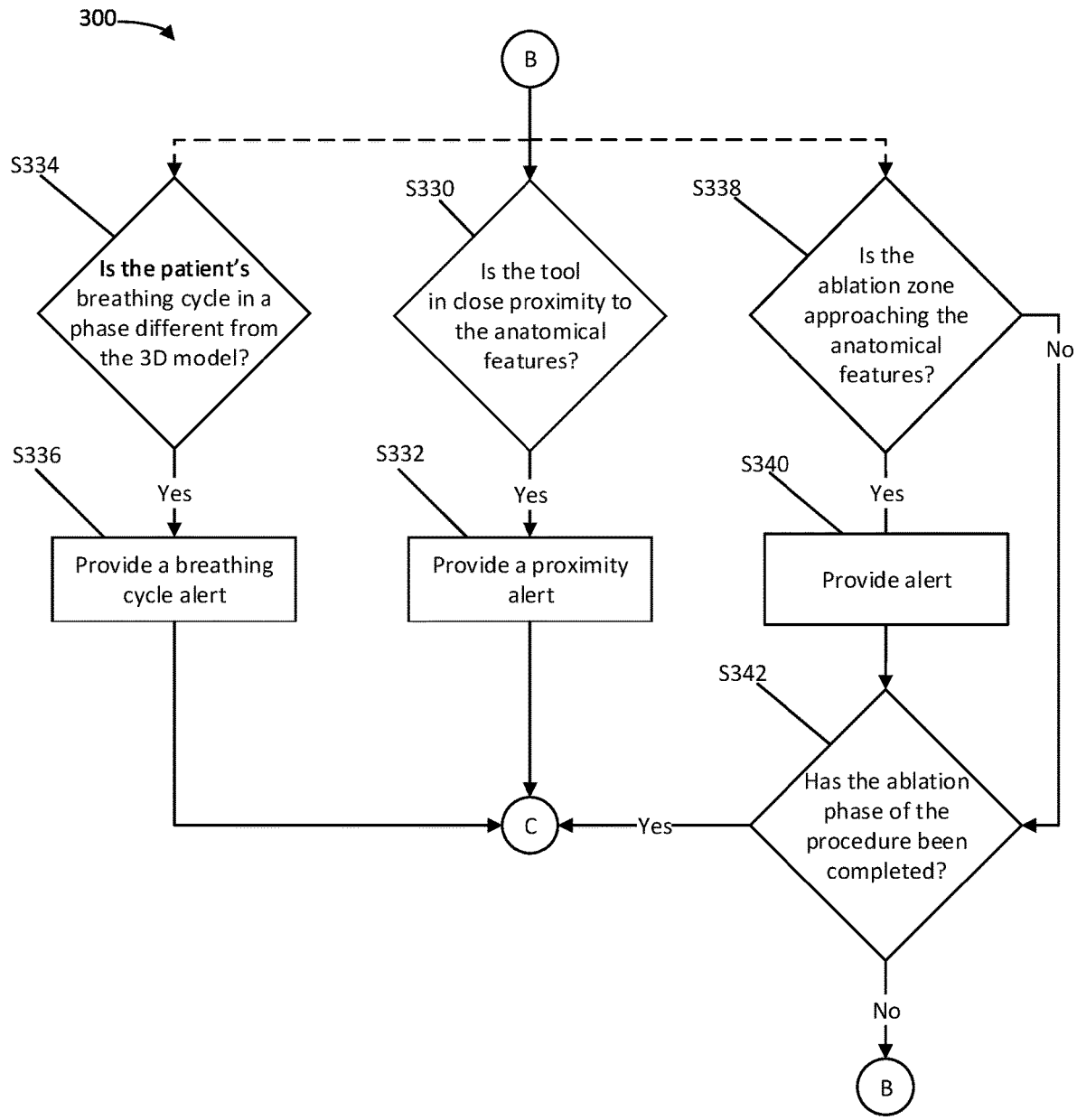

Referring now to FIGS. 3A-3C, an exemplary computer-implemented method 300 is provided for providing proximity awareness to pleural boundaries and vascular structures. Method 300 may be implemented, at least in part, by processor 204 executing application 81 stored in memory 202. Additionally, the particular sequence of steps shown in the method 300 of FIGS. 3A-3C is provided by way of example and not limitation. Thus, the steps of the method 300 may be executed in sequences other than the sequence shown in FIGS. 3A-3C without departing from the scope of the present disclosure. Further, some steps shown in the method 300 of FIGS. 3A-3C may be concurrently executed with respect to one another instead of sequentially executed with respect to one another. Method 300 may be implemented using a variety of different tools, systems, and surgical approaches. For example, method 300 may be implemented using an endobronchial navigation system, such as EMN system 10 of FIG. 1 (described above). Alternatively, method 300 may be implemented using a percutaneous surgical system, such as system 500 of FIG. 5 (described below).

In an embodiment, method 300 generally includes a planning phase, shown in FIG. 3A, followed by a navigation phase, shown in FIGS. 3B and 3C. The planning phase of method 300 may begin at step S302, where computing device 80 receives image data of the patient's chest, including the patient's lungs. As noted above, the images may be received from various imaging devices using various imaging modalities, including a CT scan, MM scan, PET scan, X-ray scan, CBCT scan, and/or any other applicable imaging modality known to those skilled in the art. For illustrative purposes, this description will use CT scan data as the image data.

At step S304, a 3D model of the patient's chest is generated. The 3D model may be based on the image data received during step S302, image data previously stored on computing device 80, and/or previously generated 3D models of the patient. The 3D model may show, among other things, the patient's lung parenchyma, such as the airways, as well as other structures such as blood vessels and lymphatic structures, among others.

Thereafter, at step S306, a location of anatomical features, such as the pleura of the patient's lungs as well as vascular structures and/or other physiological elements is determined, as described above. Multiple anatomical features may be identified. A determination of the location of the pleura and vascular structures may be based on the image data received during step S302, and/or the 3D model generated during step S304. For example, one or more image processing algorithms may be employed to detect anatomical features, such as the pleura, the esophagus, the diaphragm, the heart, and/or vascular structures. In an embodiment, a region growing algorithm similar to that used during generation of the 3D model may additionally or alternatively be used. In addition, data regarding the movement of the patient's airways during the patient's respiratory cycle may be used to compensate for differences in the detected locations of the pleural surfaces and vascular structures. Systems, devices, and methods for detecting movement of the patient's airways during the patient's respiratory cycle are further described in commonly-owned co-pending U.S. Pat. No. 10,292,619, entitled "PATIENT BREATHING MODELING", filed on Jul. 9, 2008, by Dorian Averbuch, and commonly-owned U.S. Pat. No. 7,233,820, entitled "ENDOSCOPE STRUCTURES AND TECHNIQUES FOR NAVIGATING TO A TARGET IN BRANCHED STRUCTURE", filed on Apr. 16, 2003, by Pinhas Gilboa, the entire contents of both of which are incorporated herein by reference.

At step S308, a target location is identified in the 3D model of the patient's airways. The target location may be the site where primary treatment will be performed. For example, the target location may be the site where a tumor or lesion is located. Alternatively, the target location may be a previous treatment site that requires additional treatment. The target location may be manually selected by a clinician, and/or may be automatically determined by computing device 80 and/or application 81 and reviewed by the clinician.

Depending on the type of procedure being performed, additional planning steps may be performed. For example, in a microwave ablation treatment procedure, the optional steps shown in box 350 of FIG. 3A may be performed. Thus, if the procedure being performed is a microwave ablation treatment procedure, the method proceeds to step S310 after step S308 is completed. However, if the procedure being performed is not a microwave ablation treatment procedure, the method proceeds directly to step S318, skipping steps S310-S316.

At step S310, ablation settings may be received by application 81. The ablation settings may include a power, temperature, and duration of the ablation. The ablation settings may be entered manually by the clinician, and/or may be automatically determined by computing device 80 and/or application 81 and reviewed by the clinician. Then, at step S312, application 81 may determine a projected ablation zone based on target location the ablation settings. The projected ablation zone may be a spherically shaped area centered on a point at the target location to which microwave ablation tool 104 may be navigated.

Next, at step S314, it is determined whether the projected ablation zone encroaches on the locations of the anatomical features, e.g., the pleura and vascular structures determined at step S306. In addition to actual encroachment, it may also be determined whether the projected ablation zone is close enough to the locations of the pleura and vascular structures for there to be a risk of injury. If it is determined that the projected ablation zone encroaches on the locations of the pleura and vascular structures, an alert may be provided at step S316. The alert may be in the form of a visual alert displayed on computing device 80, and/or an audible alert emitted by computing device 80. Application 81 may further identify and/or highlight portions of the pleura and/or vascular structures which may be affected by the proposed ablation zone.

As indicated in FIG. 3A, the planning phase of the surgical procedure (e.g., steps S302-S316) are executed at least once prior to the start of the navigation phase, in an embodiment. In another embodiment, the steps S302-S316 may be repeated during the navigation phase of the surgical procedure. Numerous other steps may performed during the planning phase, omitted here for purposes of brevity, but described in U.S. Pat. Nos. 9,459,770, 9,925,009, and 9,639,666, filed by Baker et al., described above.

After completion of the planning phase of the surgical procedure, the clinician may initiate the navigation phase. In the embodiment described below, an endobronchial EMN procedure is used for illustrative purposes to describe the various steps that may be performed. However, as will be appreciated by those skilled in the art, the same or similar steps may be performed using a percutaneous surgical system, such as system 500 of FIG. 5 (described below), without departing from the scope of the present disclosure.

Thus, in the illustrative embodiment, the navigation phase generally begins with the insertion of bronchoscope 50, EWC 96, and EM sensor 94 into the patient's airways. As noted above, EM sensor 94 may be included in LG 92, biopsy tool 102, and/or microwave ablation tool 104. EM sensor 94 may also be included in a surgical needle or other thoracoscopic instrument or tool. In some embodiments, EM sensor 94 may be included in a surgical tool or implement that is inserted into the patient's airways without the use of bronchoscope 50 and/or EWC 96.

With reference to FIG. 3B, thereafter, at step S318 of FIG. 3B, a position of EM sensor 94 inside the patient's chest, e.g., the patient's airways, is detected, by using, for example, EM tracking system 70. Step S318 may be iteratively repeated while EM sensor 94 is navigated about the patient's airways. In some embodiments, EM sensor 94 may not be located inside an airway but rather at some other position inside the patient's chest, such as other lung tissue, or a tumor. In embodiments where multiple tools are used concurrently, EM tracking system 70 may detect and track the positions of multiple EM sensors 94 at the same time. Similarly, in an embodiment, an EM sensor 94 may be navigated to the target location to mark the target location, and the marked target location may then be used as a point of reference and to update the registration. Further, the position of the target location within the 3D model may be updated based on, and to correspond with, the marked target location. For example, after EM sensor 94 is navigated to the target location, placement of EM sensor 94 at the target location may be confirmed using one or more imaging modalities, including a CT scan, a CBCT scan, an ultrasound scan, and/or fluoroscopy. After confirming the position of EM sensor 94 at the target location, the position of EM sensor 94 may be marked as the target location in the 3D model. That is, the previously marked target location in the 3D model may be updated to correspond with the marked target location. If desired the registration of the 3D model to the patient's airways may be updated. Regardless, having now confirmed the position of the target location and updated the 3D model accordingly, even if EM sensor 94 is moved away from the target location the position of EM sensor 94 can then be tracked relative to the updated target location in the 3D model. Thereafter, the view of the 3D model may be changed, such as by re-centering, based on the updated target location when EM sensor 94 again approaches the target location in the patient's body. After updating the position of the target location, further tracking of EM sensor 94 may be performed based on the marked position of the target location. For example, after the target location is marked, EM sensor 94 may then be tracked purely based on EM sensor 94's position in 3D space relative to the marked target location, as tracked by EM tracking system 70. That is, EM sensor 94 may be navigated to the target location, and placement of EM sensor 94 at the target location may be confirmed, by only using EM tracking system 70. Likewise, treatment procedures at the target location may be performed by only using EM tracking system 70 and the relevant treatment tool.

At step S320, a determination is made whether additional image data has been received. For example, during the navigation phase, computing device 80 may receive additional image data of the patient's lungs, for example, from a CBCT scan and/or ultrasound scan performed concurrently with, or at intervals during the navigation phase of the EMN procedure. Additionally or alternatively, data may be collected during the navigation phase, such as data relating to the position of EM sensor 94. If additional image data has been received, processing proceeds to step S322 where the 3D model is updated according to the additional data and then to step S324. If not, processing proceeds to step S324.

At step S324, a distance between the position of EM sensor 94 (detected at step S318) and the location of the anatomical features, e.g., the pleura and vascular structures (determined at step S306) is determined. Likewise, a direction between the position of EM sensor 94 and the location of the pleura and vascular structures is determined. This process may be repeated for each EM sensor 94 tracked by EM tracking system 70 and each anatomical feature for which a location is determined at step S306. For example, the distance and direction between multiple EM sensors 94 may be determined. Similarly, the distance and direction between EM sensor 94 and multiple anatomical features may be determined. In an embodiment where EM sensor 94 is being navigated towards the anatomical feature, such as the pleura, a distance and direction to the pleura may be determined. In another embodiment where EM sensor 94 is being navigated away from the anatomical feature, such as the pleura, the distance and direction from the pleura may be determined. In yet another embodiment where EM sensor 94 is between the visceral and parietal pleura, the distance and direction to one pleural surface, such as the visceral pleura, and the distance and direction from another pleural surface, such as the parietal pleura, may be determined.

Figure 4:
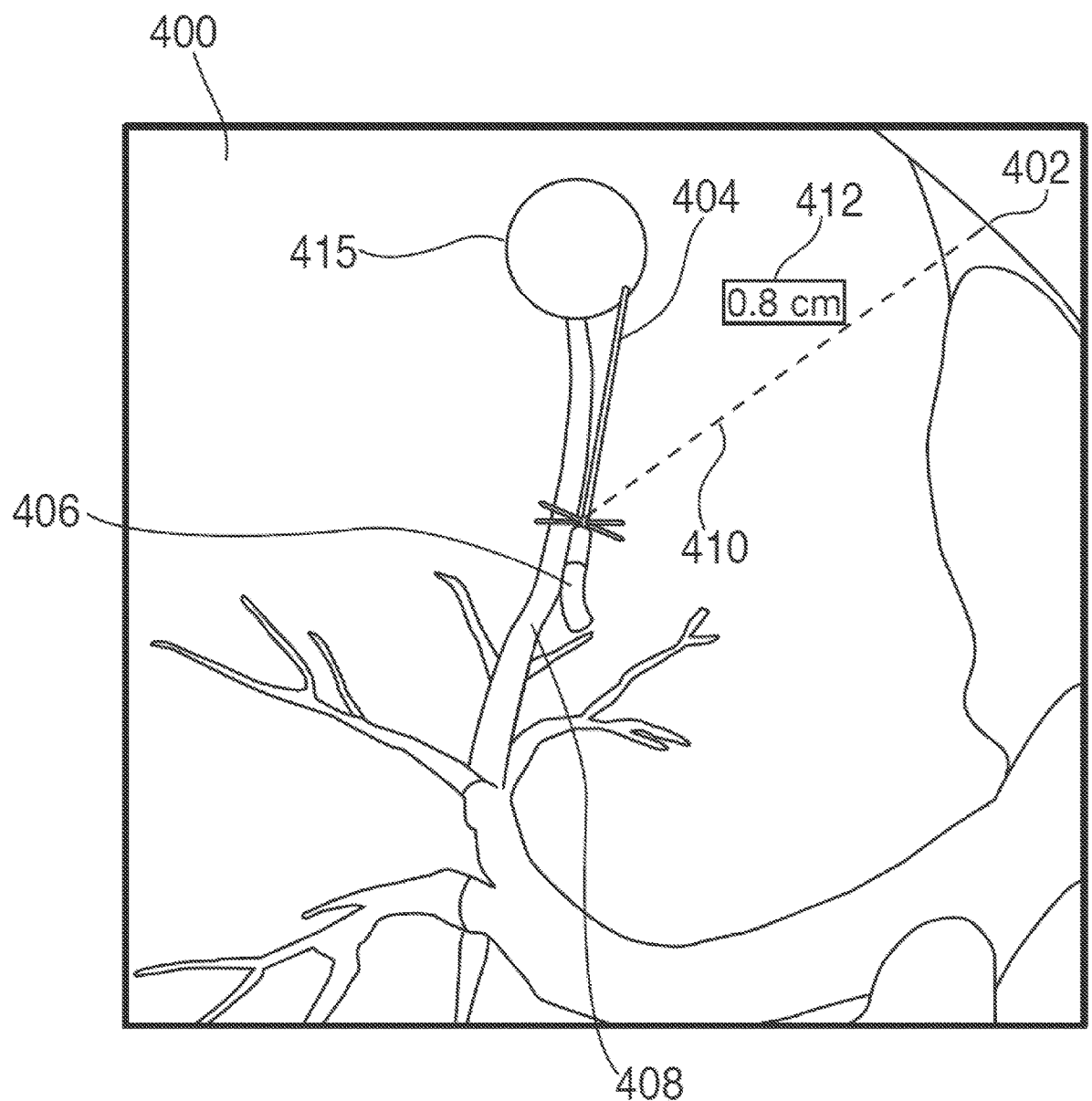
FIG. 4 is an exemplary view of a graphical user interface (GUI) for providing proximity awareness to critical structures that may be displayed by a computing device forming part of the EMN system of FIG. 1.
Figure 5:
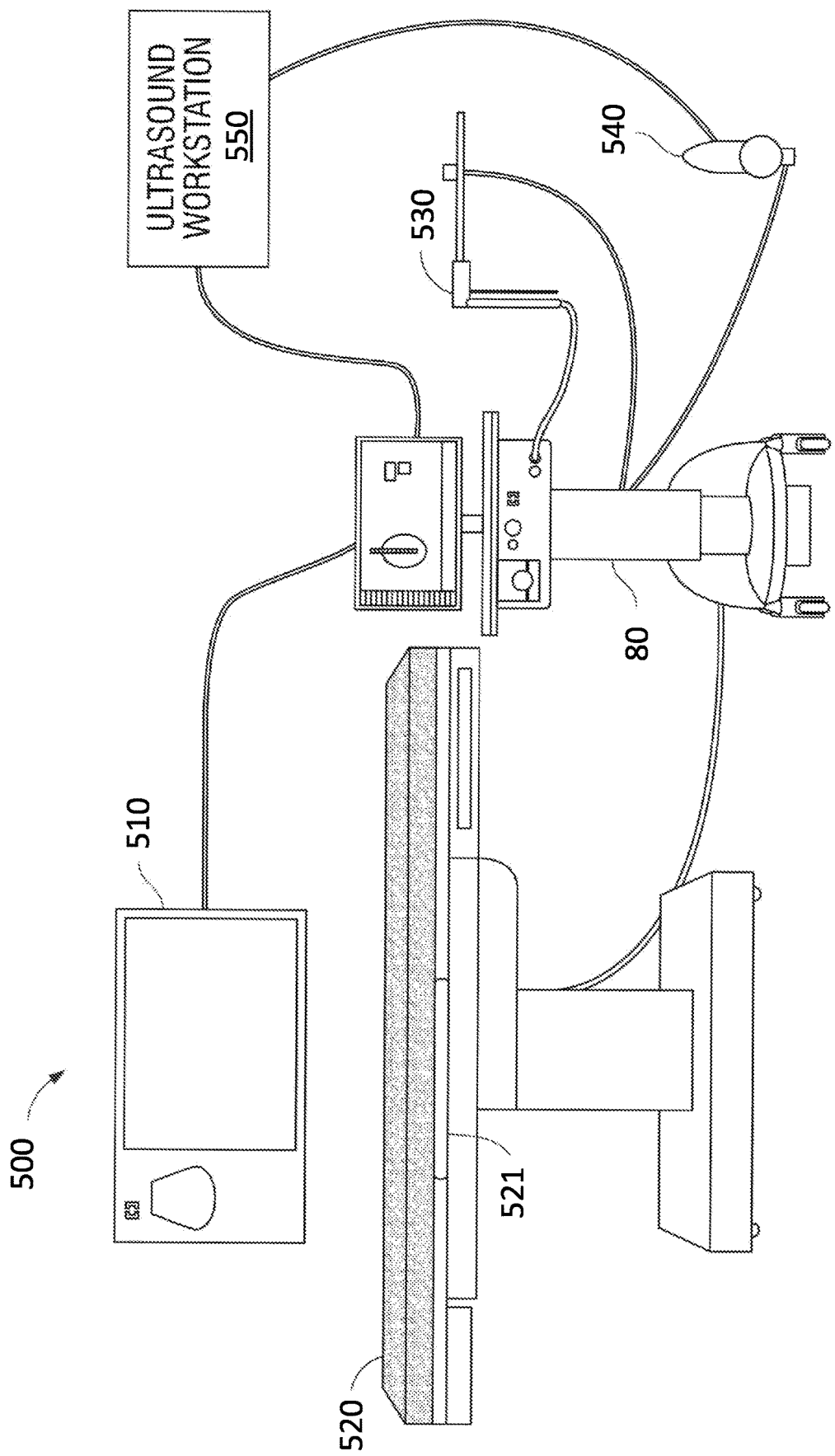
FIG. 5 is a schematic diagram of a percutaneous surgical planning and procedure system, according to an embodiment of the present disclosure.
Figure 6:
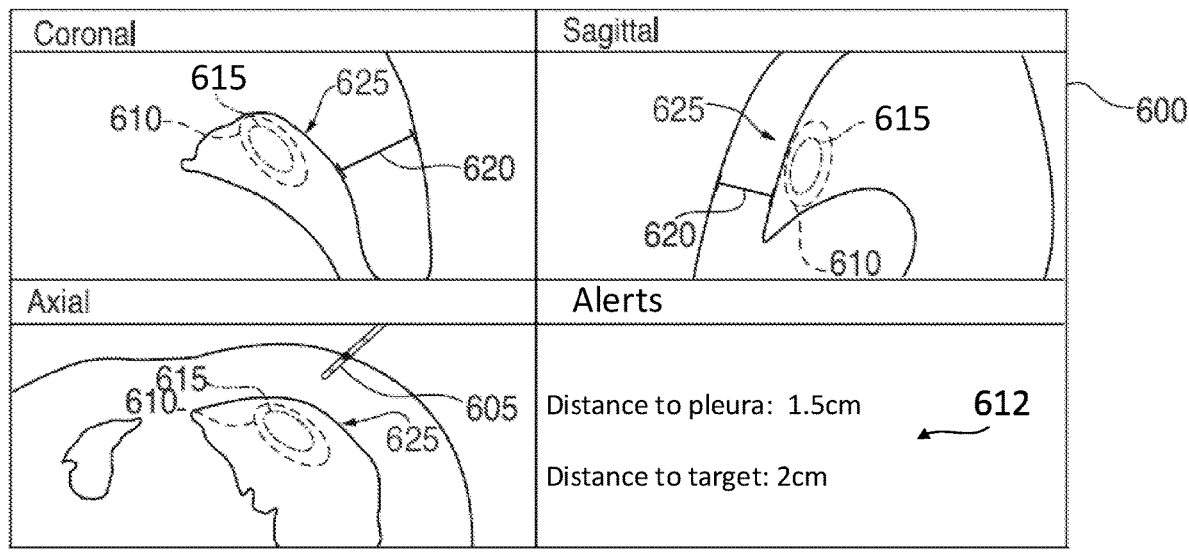
FIG. 6 is an exemplary view of a GUI for providing proximity awareness to critical structures that may be displayed by a computing device forming part of the microwave ablation system of FIG. 5.

Thereafter, at step S326, an indication of the proximity of EM sensor 94 to the location of the anatomical features, e.g., the pleura and vascular structures, is displayed. For example, a graphical user interface (GUI), an example of which is shown in FIG. 4 (described below), may be displayed by display 206 of computing device 80. Alternatively, in an embodiment where a percutaneous surgical system, such as system 500 of FIG. 5 (described below) is used, a GUI such as shown in FIG. 6 (described below) may be displayed. The indication may be provided as the distance from the closest pleural surface or vascular structure, and/or may include a direction indicator to the closest pleural surface or vascular structure, based on the determination at step S324. For example, the display may include an arrow pointing in the direction of the closest pleural surface or vascular structure, and have a distance metric, such as the distance in millimeters, to the closest pleural surface or vascular structure. The indication of the proximity of EM sensor 94 to the location of the pleura or vascular structure, including the distance and direction to the closest pleural surface and/or vascular structure may be iteratively updated as EM sensor 94 is moved and new distances and directions are determined. Similarly, a count-down indicator may be displayed, representing the distance between EM sensor 94 and the closest pleural surface and/or vascular structure. Additionally, the indication may be in the form of an audible or sensory indicator.

Next, at step S328, it is determined whether the entire procedure has been completed. For example, application 81 may determine, based on user input and/or based on automatic processing such as by analyzing the planned procedure settings and the position of the tool, whether the entire procedure has been completed. If it is determined that the entire procedure is complete, the method ends. However, if it is determined that the entire procedure has not been completed, the method proceeds to step S330.

Turning now to FIG. 3C, at step S330, a determination is made as to whether EM sensor 94 is in close proximity, such as, within a predetermined distance, to an anatomical feature, e.g., a pleural surface and/or vascular structure. If it is determined that EM sensor 94 is in close proximity to a pleural surface and/or vascular structure, a proximity alert is provided at step S332, whereafter processing returns to step S318. The proximity alert may be a visual alert displayed by application 81 and/or an audible or sensory alert provided by application 81.

In an embodiment, data regarding the patient's respiratory cycle may be used to compensate for the movement of the patient's airways during the various phases of the patient's respiratory cycle. For example, before, after, or concurrently with step S330, an optional step S334, may be performed where a determination may be made that the patient's respiratory cycle is in a particular phase, e.g., a phase different from the phase during which the image data used to generate the 3D model was collected. In such case, at step S336, an alert may be presented to the clinician that the currently displayed location of EM sensor 94 may be inaccurate, whereafter processing returns to step S318. The notification, which may be a displayed or audible message or signal, may also suggest that the clinician not navigate further for a predetermined time until the patient's respiratory cycle is in a different phase during which the location of EM sensor 94 may be accurately displayed.

Similarly, in an embodiment in which a microwave ablation tool is used, before, after, or concurrently with step S330, an optional step S338 may be performed where application 81 determines whether the actual ablation zone is approaching the anatomical features, e.g., the pleura and/or vascular structures, or a predetermined boundary-distance therefrom. For example, application 81 may, based on the ablation settings received at step S310 and a start time of the ablation procedure, determine whether the area of tissue actually being treated by microwave ablation tool 104 is approaching a predetermined boundary-distance from the locations of the pleura and/or vascular structures.

If it is determined that the actual ablation zone is approaching the predetermined boundary-distance from the locations of the pleura and/or vascular structures, an alert may be provided at step S340. The proximity alert may be a visual alert displayed by application 81 and/or an audible or sensory alert provided by application 81. However, if it is determined that the actual ablation zone is not approaching the predetermined boundary-distance from the locations of the pleura and/or vascular structures, the method proceeds to step S342 where it is determined whether the ablation phase of the procedure has been completed. If the ablation phase of the procedure has not been completed, the method returns to step S330. If the ablation phase of the procedure is complete, the method proceeds to step S318.

Similar to the above description of the planning phase, numerous steps of the navigation phase are omitted here for purposes of brevity, but are described in U.S. Patent Publication No. 2016/0000302, by Brown et al., described above.

Turning now to FIG. 4, there is shown an exemplary GUI 400 for providing proximity awareness to critical structures, according to an embodiment of the present disclosure. GUI 400 may include a view of 3D model 408, showing the location of digital marker 406 representing EM sensor 94 being navigated toward a target 415. A trajectory 404 may show the trajectory of EM sensor 94. Additionally, a proximity indicator 410 (shown as a dashed line) may indicate the direction to the nearest pleural surface 402, and a measure 412 of the distance between digital marker 406 and pleural surface 402 may be provided. As noted above, proximity awareness may also be provided to structures other than the pleura. Thus, in such embodiments, proximity indicator 410 and measure 412 may relate to such other structures.

While the above-provided embodiments are directed to providing proximity awareness to pleural surfaces and/or vascular structures, it is envisioned that the above-described system may be used to provide guidance while navigating to a pleural surface or vascular structure, for example, to inject a dye or place a marker subpleurally or proximate the pleural surface or vascular structure. Additionally, once such dyes or markers are placed, the system may be updated to provide proximity awareness to such dyes or markers similar to the above-described methods of providing proximity awareness to critical structures.

While the above-described systems, devices, and methods are directed to performing an EMN procedure, it will be appreciated by those skilled in the art that the same or similar devices, systems, and methods may be used to perform a percutaneous surgical procedure. For example, in planning a percutaneous surgical procedure, the clinician may take into account the locations of the pleura and vascular structures when deciding on which access route to use to a particular treatment location. FIG. 5 illustrates an exemplary treatment system 500 that may be used to perform such a percutaneous surgical procedure.

System 500 of FIG. 5 includes a computing device 80, a display 510, a table 520, a treatment tool 530, and an ultrasound sensor 540 connected to an ultrasound workstation 550. Similar to the computing device described above with reference to FIG. 1, computing device 80 may be, for example, a laptop computer, desktop computer, tablet computer, or other similar device. Computing device 80 may be configured to control an electrosurgical generator, a peristaltic pump, a power supply, and/or any other accessories and peripheral devices relating to, or forming part of, system 500. Display 510 is configured to output instructions, images, and messages relating to the performance of the treatment procedure. Table 520 may be, for example, an operating table or other table suitable for use during a treatment procedure, which includes an electromagnetic (EM) field generator 521. EM field generator 521 is used to generate an EM field during the treatment procedure and forms part of an EM tracking system that is used to track the positions of surgical instruments within the body of a patient. EM field generator 521 may include various components, such as a specially designed pad to be placed under, or integrated into, an operating table or patient bed. An example of such an EM tracking system is the AURORA™ system sold by Northern Digital Inc. Treatment tool 530 is a surgical instrument for percutaneously accessing and treating a target location. For example, treatment tool 530 may be an ablation probe having a microwave ablation antenna that is used to ablate tissue. While the present disclosure describes the use of system 500 in a surgical environment, it is also envisioned that some or all of the components of system 500 may be used in alternative settings, for example, an imaging laboratory and/or an office setting.

In addition to the EM tracking system, the surgical instruments may also be visualized by using ultrasound imaging. Ultrasound sensor 540, such as an ultrasound wand, may be used to image the patient's body during the treatment procedure to visualize the location of the surgical instruments, such as treatment tool 530, inside the patient's body. Ultrasound sensor 540 may have an EM tracking sensor embedded within or attached to the ultrasound wand, for example, a clip-on sensor or a sticker sensor. As described further below, ultrasound sensor 540 may be positioned in relation to treatment tool 530 such that treatment tool 530 is at an angle to the ultrasound image plane, thereby enabling the clinician to visualize the spatial relationship of treatment tool 530 with the ultrasound image plane and with objects being imaged. Further, the EM tracking system may also track the location of ultrasound sensor 540. In some embodiments, one or more ultrasound sensors 540 may be placed inside the body of the patient. EM tracking system may then track the location of such ultrasound sensors 540 and treatment tool 530 inside the body of the patient. Ultrasound workstation 550 may be used to configure, operate, and view images captured by ultrasound sensor 540.

Various other surgical instruments or surgical tools, such as LigaSure™ devices, surgical staples, etc., may also be used during the performance of a treatment procedure. In embodiment where treatment tool 530 is an ablation probe, the ablation probe is used to ablate a lesion or tumor (hereinafter referred to as a "target") by using electromagnetic radiation or microwave energy to heat tissue in order to denature or kill cancerous cells. The construction and use of a system including such an ablation probe is more fully described in U.S. Pat. No. 10,624,697, entitled MICROWAVE ABLATION SYSTEM, filed on Aug. 26, 2014, by Dickhans, U.S. Pat. No. 9,247,992 by Latkow et al., described above, and U.S. Pat. No. 9,119,650, entitled MICROWAVE ENERGY-DELIVERY DEVICE AND SYSTEM, filed on Mar. 15, 2013, by Brannan et al., the contents of all of which is hereby incorporated by reference in its entirety.

The location of treatment tool 530 within the body of the patient may be tracked during the treatment procedure. An example method of tracking the location of treatment tool 530 is by using the EM tracking system, which tracks the location of treatment tool 530 by tracking sensors attached to or incorporated in treatment tool 530. Various types of sensors may be used, such as a printed sensor, the construction and use of which is more fully described in co-pending US Patent Publication No. 2016/0174873, filed Oct. 22, 2015, by Greenburg et al., the entire contents of which is incorporated herein by reference. A percutaneous treatment system similar to the above-described system 500 is further described in co-pending US Patent Publication Nos. 2016/0317224, 2016/0317230, 2016/0317231, 2016/0317225, and 2016/0317229, all filed on Apr. 15, 2016, by Girotto et al., the entire contents of each of which is incorporated herein by reference.

FIG. 6 shows an exemplary GUI 600 for providing proximity awareness to critical structures, according to an embodiment of the present disclosure. GUI 600 may include multiple views of the 3D model of the patient's chest. For example, coronal, sagittal, and/or axial views may be displayed. Each view may include a representation of the patient's lungs 625. In addition, one or more of the views of GUI 600 may include a representation of the target 615 and a projected ablation zone 610. GUI 600 may further include a distance indicator 620 and a representation of a surgical tool 605. As noted above, application 81 may display indicators 612 of a distance between surgical tool 605 and target 615, and/or a distance between surgical tool 605 and the closest critical structure.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure. While the preceding embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well. Additionally, the same or similar methods as those described herein may be applied to navigating in other parts of the body, such as the chest areas outside of the lungs, the abdomen, pelvis, joint space, brain, spine, etc., to identify critical structures and provide proximity awareness to critical structures in such other parts of the body.

With respect to memory 202 described above in connection with FIG. 2, the memory 202 may include any non-transitory computer-readable storage media for storing data and/or software that is executable by processor 204 and which controls the operation of computing device 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with computing device 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Further aspects of image and data generation, management, and manipulation useable in either the planning or navigation phases of an EMN procedure are more fully described in commonly-owned U.S. Patent Publication No. 2016/0000414, entitled "METHODS FOR MARKING BIOPSY LOCATION", filed on Jun. 29, 2015, by Brown; U.S. Patent Publication No. 2016/0000517, entitled "INTELLIGENT DISPLAY", filed on Jun. 29, 2015, by Kehat et al.; U.S. Pat. No. 9,727,986, entitled "UNIFIED COORDINATE SYSTEM FOR MULTIPLE CT SCANS OF PATIENT LUNGS", filed on Jul. 1, 2015, by Greenburg; U.S. Pat. No. 10,159,447, entitled "ALIGNMENT CT", filed on Jul. 2, 2015, by Klein et al.; U.S. Pat. No. 9,633,431, entitled "FLUOROSCOPIC POSE ESTIMATION", filed on May 29, 2015, by Merlet; U.S. Pat. No. 9,836,848, entitled "SYSTEM AND METHOD FOR SEGMENTATION OF LUNG", filed on Jun. 30, 2015, by Markov et al.; and U.S. Patent Publication No. 2016/0000520, entitled "SYSTEM AND METHOD OF PROVIDING DISTANCE AND ORIENTATION FEEDBACK WHILE NAVIGATING IN 3D", filed on Jul. 2, 2015, by Lachmanovich et al., the contents of each of which are hereby incorporated by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for providing proximity awareness to an anatomical feature while navigating inside a patient's chest, the method comprising:
   determining a location of the anatomical feature based on at least one of received image data of the patient's chest or a 3D model of the patient's chest;
   tracking a position of a microwave ablation device configured to deliver energy to tissue to create a growing ablation zone;
   indicating a proximity of the microwave ablation device relative to the anatomical feature, based on the tracked position of the microwave ablation device inside the patient's chest;
   tracking a position of a tool;
   indicating a proximity of the tool relative to the anatomical feature and a proximity of the tool relative to the microwave ablation device; and
   determining whether a boundary of the growing ablation zone created by the microwave ablation device is approaching the anatomical feature by determining whether the boundary of the growing ablation zone is approaching a predetermined distance from the anatomical feature.

2. The method of claim 1, further comprising:
   determining whether the microwave ablation device is within a predetermined distance from the anatomical feature; and
   providing a proximity alert, in response to a determination that the microwave ablation device is within the predetermined distance from the anatomical feature.

3. The method of claim 2, further comprising receiving data corresponding to movement of the patient's chest based on the patient's respiratory cycle, and wherein determining whether the microwave ablation device is within the predetermined distance from the anatomical feature includes determining whether the microwave ablation device is within the predetermined distance from the anatomical feature based on the data corresponding to movement of the patient's chest.

4. The method of claim 1, further comprising receiving data corresponding to movement of the patient's chest based on the patient's respiratory cycle, and wherein determining the location of the anatomical feature includes determining the location of the anatomical feature based on the data corresponding to the movement of the patient's chest.

5. The method of claim 1, further comprising:
receiving image data of the patient's chest; and
generating the 3D model based on the received image data.

6. The method of claim 1, wherein indicating the proximity of the microwave ablation device relative to the anatomical feature includes displaying a value corresponding to a distance between the microwave ablation device and the anatomical feature, or an icon corresponding to a direction of the microwave ablation device relative to the anatomical feature.

7. The method of claim 1, further comprising providing an alert when a determination is made that the ablation zone created by the microwave ablation device is approaching the anatomical feature.

8. A system for providing proximity awareness to an anatomical feature while navigating inside a patient's chest, the system comprising:
a microwave ablation device configured to be inserted into the patient's chest and to create a growing ablation zone; and
a computing device including a processor and a memory storing instructions which, when executed by the processor, cause the computing device to:
determine a location of the anatomical feature based on at least one of received image data of the patient's chest or a 3D model of the patient's chest;
track a position of the microwave ablation device inside the patient's chest;
indicate a proximity of the microwave ablation device relative to the anatomical feature, based on the tracked position of the microwave ablation device inside the patient's chest; and
determine whether a boundary of the growing ablation zone created by the microwave ablation device is approaching the anatomical feature by determining whether the boundary of the growing ablation zone is approaching a predetermined distance from the anatomical feature.

9. The system of claim 8, wherein the instructions further cause the computing device to:
determine whether the microwave ablation device is within a predetermined distance from the anatomical feature; and
provide a proximity alert when a determination is made that the microwave ablation device is within the predetermined distance from the anatomical feature.

10. The system of claim 9, wherein the instructions further cause the computing device to receive data corresponding to movement of the patient's chest based on the patient's respiratory cycle, and wherein the computing device determines whether the microwave ablation device is within the predetermined distance from the anatomical feature by determining whether the microwave ablation device is within the predetermined distance from the anatomical feature based on the data corresponding to movement of the patient's chest.

11. The system of claim 8, wherein the instructions further cause the computing device to receive data corresponding to movement of the patient's chest based on the patient's respiratory cycle, and wherein the computing device determines the location of the anatomical feature by determining the location of the anatomical feature based on the data corresponding to the movement of the patient's chest.

12. The system of claim 8, wherein the instructions further cause the computing device to:
receive image data of the patient's chest; and
generate the 3D model based on the received image data.

13. The system of claim 8, wherein the indication of the proximity of the microwave ablation device relative to the anatomical feature includes a value corresponding to a distance between the microwave ablation device and the anatomical feature, or an icon corresponding to a direction of the microwave ablation device relative to the anatomical feature.

14. The system of claim 8, wherein the instructions further cause the computing device to:
provide an alert when a determination is made that the ablation zone created by the microwave ablation device is approaching the anatomical feature.

15. The system of claim 8, wherein the instructions further cause the computing device to:
track a position of a tool; and
indicate a proximity of the tool relative to the microwave ablation device and a proximity of the tool relative to the anatomical feature.

16. A non-transitory computer-readable storage medium storing instructions which, when executed by a processor, cause a computer to:
receive image data or a 3D model of a patient's chest;
determine a location of an anatomical feature based on at least one of the received image data or the generated 3D model;
track a position of a microwave ablation device and a position of a tool inside the patient's chest, wherein the microwave ablation device is configured to deliver energy to tissue to create a growing ablation zone;
indicate a proximity of the microwave ablation device relative to the anatomical feature, based on the tracked position of the microwave ablation device inside the patient's chest;
indicate a proximity of the microwave ablation device relative to the tool or a proximity of the tool relative to the anatomical feature; and
determine whether a boundary of the growing ablation zone created by the microwave ablation device is approaching the anatomical feature by determining whether the boundary of the growing ablation zone is approaching a predetermined distance from the anatomical feature.

17. The non-transitory computer-readable storage medium according to claim 16, wherein the instructions further cause the computer to:
determine whether the microwave ablation device is within a predetermined distance from the anatomical feature; and
provide a proximity alert when a determination is made that the microwave ablation device is within the predetermined distance from the anatomical feature.

18. The non-transitory computer-readable storage medium according to claim 16, wherein the indication of the proximity of the microwave ablation device relative to the anatomical feature includes a value corresponding to a distance between the microwave ablation device and the anatomical feature, or an icon corresponding to a direction of the microwave ablation device relative to the anatomical feature.

19. The non-transitory computer-readable storage medium according to claim 16, wherein the instructions further cause the computer to:
provide an alert when a determination is made that the ablation zone created by the microwave ablation device is approaching the anatomical feature.

20. The non-transitory computer-readable storage medium according to claim 16, wherein the instructions further cause the computer to electromagnetically track the position of at least one of the microwave ablation device and the tool inside a patient's chest.

* * * * *